(12) United States Patent
Osborne (10) Patent No.: US 11,730,740 B2
(45) Date of Patent: Aug. 22, 2023

(54) LAURETH-4 CONTAINING TOPICAL FORMULATIONS

(71) Applicant: ARCUTIS BIOTHERAPEUTICS, INC., Westlake Village, CA (US)

(72) Inventor: David W. Osborne, Fort Collins, CO (US)

(73) Assignee: ARCUTIS BIOTHERAPEUTICS, INC., Westlake Village, CA (US)

(*) Notice: Subject to any disclaimer, the term of this patent is extended or adjusted under 35 U.S.C. 154(b) by 48 days.

(21) Appl. No.: 17/443,699

(22) Filed: Jul. 27, 2021

(65) Prior Publication Data
US 2022/0031705 A1 Feb. 3, 2022

Related U.S. Application Data

(60) Provisional application No. 63/057,503, filed on Jul. 28, 2020.

(51) Int. Cl.
| | | |
|---|---|---|
| *A61K 31/519* | (2006.01) | |
| *A61K 9/00* | (2006.01) | |
| *A61K 9/08* | (2006.01) | |
| *A61K 31/5377* | (2006.01) | |
| *A61K 31/573* | (2006.01) | |
| *A61K 38/13* | (2006.01) | |
| *A61K 47/10* | (2017.01) | |
| *A61K 47/20* | (2006.01) | |

(52) U.S. Cl.
CPC .......... *A61K 31/519* (2013.01); *A61K 9/0014* (2013.01); *A61K 9/08* (2013.01); *A61K 31/5377* (2013.01); *A61K 31/573* (2013.01); *A61K 38/13* (2013.01); *A61K 47/10* (2013.01); *A61K 47/20* (2013.01)

(58) Field of Classification Search
CPC ...... A61K 31/519; A61K 9/0014; A61K 9/08; A61K 31/5377; A61K 31/573; A61K 38/13; A61K 47/10; A61K 47/20
See application file for complete search history.

(56) References Cited

U.S. PATENT DOCUMENTS

| | | |
|---|---|---|
| 3,711,602 A | 1/1973 | Herschler |
| 3,934,013 A | 1/1976 | Poulsen |
| 9,422,300 B2 | 8/2016 | Sun et al. |
| 9,527,851 B2 | 12/2016 | Zhang et al. |
| 10,023,577 B2 | 7/2018 | Sun et al. |
| 10,150,770 B2 | 12/2018 | Sun et al. |
| 10,428,074 B2 | 10/2019 | Zhang et al. |
| 10,786,507 B2 | 9/2020 | Lu et al. |
| 2017/0044171 A1 | 2/2017 | Zhang et al. |
| 2019/0060311 A1 | 2/2019 | Shanler et al. |
| 2019/0127364 A1 | 5/2019 | Kozak et al. |
| 2020/0197397 A1* | 6/2020 | Arkin ................... A61K 9/0014 |
| 2020/0276109 A1* | 9/2020 | Xi ........................ A61K 9/1623 |

FOREIGN PATENT DOCUMENTS

| | | | |
|---|---|---|---|
| WO | 2011076209 A2 | 6/2011 | |
| WO | WO-2020025910 A1 * | 2/2020 | ............. A61K 31/69 |

OTHER PUBLICATIONS

Heather A.E. Benson "Transdermal Drug Delivery: Penetration Enhancement Techniques" Current Drug Delivery, (2005), 2(1):23-33.
David W. Osborne et al. "Skin Penetration and Permeation Properties of Transcutol®—Neat or Diluted Mixtures" AAPS PharmSciTech, (2018), 19(8):3512-3533.
Rong-Kun Chang et al. "Generic Development of Topical Dermatologic Products: Formulation Development, Process Development, and Testing of Topical Dermatologic Products" AAPS Journal, (2012), 15(1):41-52.
David W. Osborne et al. "Skin Penetration Enhancers Cited in the Technical Literature" Pharmaceutical Technology (1997), 21:58-66.
Wu-Wei Shen et al. "Effect of nonionic surfactants on percutaneous absorption of salicylic acid and sodium salicylate in the presence of dimethyl sulfoxide" J. Pharm. Sci, (1976), 65(12):1780-1783.
Bruce J. Aungst et al. "Enhancement of naloxone penetration through human skin in vitro using fatty acids, fatty alcohols, surfactants, sulfoxides and amides" International Journal of Pharmaceutics, (1986), 33(1-3):225-234.
International Search Report and the Written Opinion of the International Searching Authority, issued in corresponding International Application No. PCT/US2021/071019, dated Oct. 22, 2021, 12 pages.
Notification Concerning Transmittal of International Preliminary Report On Patentability issued in International Application No. PCT/US2021/071019, dated Feb. 9, 2023, 7 pages.

* cited by examiner

*Primary Examiner* — Brandon J Fetterolf
*Assistant Examiner* — Manahil Mirghani Ali Abdalhameed
(74) *Attorney, Agent, or Firm* — Rothwell, Figg, Ernst & Manbeck, P.C.

(57) ABSTRACT

The present invention is a method and composition comprising laureth-4 in topical formulations, wherein the laureth-4 increases the penetration of active ingredients across the skin. In a particularly preferred embodiment, the active ingredient is SHR0302.

16 Claims, 6 Drawing Sheets

LAURETH-4 CONTAINING TOPICAL FORMULATIONS

CROSS REFERENCE TO RELATED APPLICATIONS

The present application claims priority to U.S. Provisional Application No. 63/057,503 filed on Jul. 28, 2020, the disclosure of which is incorporated herein in its entirety by reference.

FIELD OF THE INVENTION

The subject matter disclosed herein generally relates to topical formulations containing laureth-4. Specifically, the disclosure addresses the surprising discovery that laureth-4 acts as a penetration enhancer in the presently disclosed and claimed topical formulations.

BACKGROUND OF THE INVENTION

The epidermal barrier has several functions including maintaining water balance, reducing oxidative stress, protecting against foreign substances such as microbes and antigens and protecting against ultraviolet light damage. The entire epidermis is involved in the epidermal barrier but the stratum corneum is mainly responsible for many of these functions. Many topically administered drugs do not have the ability to adequately penetrate the stratum corneum to achieve maximum clinical efficacy. In these cases, modulations of the skin penetration profiles of these drugs and skin barrier manipulations are necessary. A skin penetration enhancement can be achieved either chemically, physically or by use of appropriate formulations.

Skin penetration enhancement is achieved mechanistically by optimization of drug and vehicle properties and/or modification of the stratum corneum (H. A. E. Benson "Transdermal Drug Delivery Penetration Enhancement Techniques" Current Drug Delivery 2, 23-33, 2005). Optimization of drug and vehicle properties includes selecting the most potent active in a pharmacological class that has a molecular weight nearer 300 Daltons than 500 Daltons. Synthesis of a prodrug for actives that are too hydrophilic (log $P_{octanol/water}$<2.5), or forming ion-pairs with a charged active to facilitate partitioning into the stratum corneum are additional examples of strategies to optimize drug and vehicle properties. Similar strategies to forming ion pairs include developing eutectic systems, complexation of the drug using materials such cyclodextrins or the formulation of complex vehicles such as liposomes, vesicles or nano-technology formulations. One of the earliest recognized strategies for optimizing topical drug and vehicle properties was the use of solvents, especially propylene glycol (PG), to balance the concentration of dissolved active in the formulation while maximizing the chemical potential, i.e. thermodynamic driving force, of the drug.

Solvents such as propylene glycol (PG), N-methylpyrrolidone (NMP), ethanol, and dimethyl sulfoxide (DMSO) have long been used to optimize drug-vehicle properties to enhance both penetration into the stratum corneum and permeation across the stratum corneum into the viable epidermis. Since 2005 diethylene glycol monoethyl ether (DEGEE) has been added to the list of solvents that optimize drug-vehicle properties of topical prescription products established by the US Food and Drug Administration as safe and effective. It has also long been recognized that these solvents readily permeate and modify the stratum corneum.

Although solvents can effectively be used to enhance skin penetration/permeation of drugs, to maximize the amounts of drug that crosses the skin requires blending a solvent with fatty alcohols, fatty acids or fatty acid ester adjuvants such as nonionic surfactants.

This synergistic skin penetration was described for PG in 1976 (U.S. Pat. No. 3,934,013, Poulsen, issued Jan. 20, 1976), for NMP in 2011 (WO 2011/07629 A2, Peters son, published Jun. 30, 2011) and for DMSO in 1973 (U.S. Pat. No. 3,711,602A, Herschler, issued Jan. 16, 1973). An article published in 2018 (D W Osborne and J Musakhanian, AAPS Pharm SciTech. 19(8):3512-3533 (2018) DOI: 10.1208/s12249-018-1196-8) provided a comprehensive review of skin penetration enhancement literature of DEGEE when combined with fatty alcohols, fatty acids, or fatty acid ester adjuvants.

During review of the published skin penetration enhancer data, it becomes apparent that an in vitro permeation testing (IVPT) experimental artifact has often been mistaken for skin penetration enhancement. This artifact occurs when excised skin mounted on an in vitro diffusion cell (typically a Franz vertical diffusion cell) with an infinite dose of liquid or semisolid. For our purposes we define an infinite dose as anything over 20 µl of formulation per 1 $cm^2$ surface area of skin. The artifact is caused by the applied dose extracting barrier lipids from the stratum corneum over the time course of the experiment (typically 24 to 48-hours). Thus, the barrier properties of the tissue are reduced due to applying too much product to the surface of the skin. This results in the skin penetration enhancement factor reported for the formulation being exaggerated, sometimes by 20 to 100-fold. The magnitude of this artifact is further increased when an infinite dose is applied to excised rodent or rabbit skin compared to mounting human skin (typically dermatomed to a thickness of ~500 microns) on the IVPT diffusion cell. When applied as an infinite dose, topical solvents and fatty acid ester surfactants are the topical excipients that can greatly exaggerate IVPT flux values. Although any clinically nonrelevant dose (>20 µl) can cause this artifact, doses of 100 µl/$cm^2$ or more of a liquid or semisolid formulation containing solvents or surfactants will quickly and efficiently extract skin barrier lipids and exaggerate appearance of active in the receptor solution of the in vitro diffusion cell.

In part, because this artifact was so prevalent in the skin penetration enhancer literature of the 1980s and 1990s, the FDA Dermatology Division did not accept IVPT results as supporting data for topical product registrations prior to about 2010. In January 2012, four of the US Food and Drug Administration's key scientists published a paper entitled "Generic Development of Topical Dermatologic Products: Formulation Development, Process Development, and Testing of Topical Dermatologic Products." In that seminal publication the authors state " . . . a finite dose technique (i.e., ~3 to 5 mg/$cm^2$) is considered more relevant than infinite dose design as it better represents the clinical situation for topical drug products . . . . Data generated from in vitro permeation studies using excised human skin give a good prediction of in vivo bioavailability and bioequivalence and provide a practical surrogate to clinical bioequivalence studies."

In the 1997 publication Skin Penetration enhancers Cited in the Technical Literature, laureth-4 (listed as Brij 30) had two citations, a Shen 1976 citation (WW Shen et. al. J. Pharm Sci 65(12)1780-1783 (1976) doi.org/10.1002/jps.2600651222) and an Aungst 1986 citation (B J Aungst et. al. International journal of pharmaceutics 33(1-3) 225-234 (1986) doi.org/10.1016/0378-5173(86)90057-8). Shen et. al.

tested fifteen separate nonionic surfactants (10% w/w), that were incorporated into white petrolatum USP ointment base containing 10% (w/w) salicylic acid with 10% (w/w) dimethyl sulfoxide (DMSO). Percutaneous absorption was determined from blood salicylate levels in New Zealand white rabbits at regular intervals for 8 hr following application of 5.0 grams of the ointment to a 6.4×12.7 $cm^2$ area of skin. Percutaneous absorption of salicylic acid was increased significantly when sorbitan monopalmitate, sorbitan trioleate, poloxamer 231, poloxamer 182, polyoxyethylene 4 lauryl ether (laureth-4), polyoxyethylene 2 oleyl ether, or polyoxyl 8 stearate was added to the ointment containing dimethyl sulfoxide, salicylic acid, and white petrolatum. It should be noted that Shen used in vivo testing following infinite dosing to rabbit skin.

Aungst et. al. screened various chemicals as penetration enhancers by adding 10% adjuvant to propylene glycol (PG). Fatty acids and fatty alcohols were very effective promoters of naloxone flux. Maximum flux was with C12 saturated adjuvants in both the acid (235.2 $\mu g/cm^2$-hr for lauric acid) and alcohol (45.8 $\mu g/cm^2$-hr for lauryl alcohol) series, and for C18 unsaturated acid (103.0 $\mu g/cm^2$-hr for linolenic acid 18:2) and alcohol (116.3 $\mu g/cm^2$-hr for linolenyl alcohol) adjuvants. Other effective skin penetration enhancers included pelargonic acid (201.9±65.4 $\mu g/cm^2$-hr), capric acid (187.9±67.5 $\mu g/cm^2$-hr), propylene glycol laurate 43.8±5.5 $\mu g/cm^2$-hr) and laureth-4 (34.5±8.3 $\mu g/cm^2$-hr). This excised human skin experiment used infinite dosing (278 $\mu l/cm^2$) to compare 64 adjuvants for their ability to increase the in vitro flux of naloxone from PG. The control of PG alone (without added adjuvant) had a naloxone flux value of 1.6±0.4 $\mu g/cm^2$-hr.

In the 44 years since Shen first published that laureth-4 increased the percutaneous absorption of salicylic acid in rabbits, one photodynamic drug/device combination product and three topical drug products have been approved by the FDA that contain laureth-4. None of the three topical drug products use laureth-4 as a skin permeation enhancer. LAC-HYDRIN Cream (1.1% laureth-4) and LAC-HYDRIN Lotion (1.3% laureth-4) treat dry skin (xerosis) and are not designed to promote delivery past the stratum corneum, the target tissue for treating dry skin. The third approved product is VELTIN Gel (3% laureth-4), a dual-active gel that combines clindamycin phosphate and tretinoin for the treatment of acne. Laureth-4 and propylene glycol are used in this product to increase the solubility of tretinoin to 0.025%. Clindamycin phosphate is readily soluble in water without the addition of laureth-4 as a solubilizing agent. A formulator would not add a skin penetration enhancer to a topical clindamycin due to the clear warning in the VELTIN Gel label that systemic absorption of clindamycin could cause severe colitis that may result in death.

SUMMARY OF THE INVENTION

In accordance with one embodiment of the invention, it has surprisingly been discovered that the addition of laureth-4 to a topical formulation of the novel JAK inhibitor SHR0302 significantly increases the skin permeation of SHR0302. In some instances, the increase is a 5-fold to 30-fold increase in skin permeation as compared to a topical formulation without laureth-4.

In certain embodiments of the present invention, a topical pharmaceutical composition comprising a JAK inhibitor, laureth-4, and a solvent is provided. In preferred embodiments, the JAK inhibitor is SHR0302 (also known as ARQ-250).

The pharmaceutical composition can comprise a JAK inhibitor in an amount of about 0.1 to about 1.0% w/w. The pharmaceutical composition can comprise laureth-4 in an amount of about 0.5 to about 5% w/w. The pharmaceutical composition can further comprise dimethyl sulfoxide. Additionally, the pharmaceutical composition can comprise an antioxidant, a preservative, an emulsifier, a moisturizer, or a thickener.

The topical pharmaceutical composition can be selected from the group consisting of an oil-in-water emulsion, a water-in-oil emulsion, a microemulsion, a nanoemulsion, a foam, a spray, a hydrophilic ointment, or a hydrophobic ointment.

The topical pharmaceutical composition can further comprise a corticosteroid, timolol, methotrexate, or cyclosporine.

The topical pharmaceutical composition can enhance skin permeation by 5-fold to 30-fold relative to a topical pharmaceutical formulation without laureth-4 as measured by in vitro permeation testing.

In certain embodiments of the present invention, a method of treating an inflammatory skin disease, disorder, or condition in a subject in need thereof is provided. The method comprises topically administering to the subject a pharmaceutical composition comprising a JAK inhibitor, laureth-4, and a solvent.

The inflammatory skin disease, disorder, or condition can be one of atopic dermatitis, rosacea, psoriasis, seborrheic dermatitis, vitiligo, eczema, or alopecia areata.

The pharmaceutical compositions can be administered to the subject one or more times per day.

The method can comprise administration of the JAK inhibitor, SHR0302. The JAK inhibitor can be present in the pharmaceutical composition in an amount of about 0.1 to about 1.0% w/w. Laureth-4 can be present in the pharmaceutical composition in an amount of about 0.5 to about 5% w/w. The method of administration can comprise administering a pharmaceutical composition comprising dimethyl sulfoxide. Further, the pharmaceutical composition further comprising a corticosteroid, timolol, methotrexate, or cyclosporine.

The method of administration to a subject can result in skin penetration of the topical pharmaceutical composition that is enhanced by 5-fold to 30-fold relative to a topical pharmaceutical formulation without laureth-4 as measured by in vitro permeation testing.

In certain embodiments, a method for enhancing the skin penetration in a subject of a topical pharmaceutical formulation is provided. The method comprises preparing a formulation comprising a JAK inhibitor, laureth-4 and a solvent. In the method, the skin penetration of the topical pharmaceutical composition is enhanced by 5-fold to 30-fold relative to a topical pharmaceutical formulation without laureth-4.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein.

FIG. 2 illustrates I

$C_{20}H_{42}O_5$ and has a molecular weight of 362.5 g/mol. The structure of laureth-4 is as follows:

Laureth-4 is a synthetic polymer that is commonly used as a surfactant and emulsifier in several personal care products, including cosmetics, shampoos, soaps, deodorants, and moisturizing products. For the past 45 years, laureth-4 has been known in the scientific literature as only a nominal penetration enhancer. However, in the present invention, laureth-4 surprisingly functions as a penetration enhancer. In particular, it has been surprisingly found that laureth-4 acts as skin penetration enhancer in the topical formulations of the present invention.

Janus kinase inhibitors (JAK inhibitors) are a class of compounds that function by inhibiting the activity of one or more enzymes in the JAK family (e.g., JAK1, JAK2, JAK3, or Tyk2). These compounds are thought to work by interfering with the JAK-STAT signaling pathway, which plays a central role in immune system function. Many inflammatory cytokines and other signaling molecules rely on the JAK pathway, and specifically JAK1. It has previously been shown that inhibition of JAK1 has been shown to treat a range of inflammatory diseases, including rheumatoid arthritis, psoriasis, Crohn's disease, and eczema. There is particular interest in developing topical formulations of a JAK inhibitor for the treatment of inflammatory skin conditions.

In a preferred embodiment, the JAK1 inhibitors are those disclosed in U.S. Pat. No. 9,527,851, which is hereby incorporated by reference. In a particularly preferred embodiment, the JAK1 inhibitor is (3 aR,5 S,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide, which is also known as SHR0302 or ARQ-250. The structure of SHR0302 is:

SHR0302 is a potent small molecule inhibitor of JAK 1 that has been shown to have a high selectively for JAK1 over JAK2, and thus has the potential to treat inflammatory diseases without causing the hematopoietic adverse effects, such as anemia, thrombocytopenia, and neutropenia, associated with JAK2 inhibition. It is contemplated that topical formulations comprising SHR0302 may be effective in the treatment of inflammatory skin diseases, disorders, and conditions including, but not limited to: atopic dermatitis, rosacea, psoriasis, seborrheic dermatitis, vitiligo, eczema, and alopecia areata.

It is also contemplated that other JAK inhibitors may also be useful in the treatment of inflammatory skin diseases, disorders, and conditions and thus may be incorporated into the inventive topical formulations. Examples of JAK inhibitors that may be incorporated into the inventive formulations include ruxolitinib, tofacitinib, ocalcitinib, baricitinib, peficitinib, fedratinib, upadacitinib, filgotinib, cerdulatinib, gandotinib, lestaurtinib, momelotinib, pacritinib, abrocitinib, cucurbitacin I, decernotinib, solcitinib, CHZ868, CYT387, TG101348, AZD1480, R348, VX-509, GLPG0634, SKD2586148, AC-430, BMS-911543, or PF-04965842.

The topical formulations of the present invention include a JAK inhibitor, laureth-4, and a solvent. In preferred embodiments, the JAK inhibitor is SHR0302. In preferred embodiments, the JAK inhibitor is present in an amount of about 0.01 to about 1.0% w/w, about 0.05 to about 1.0% w/w, about 0.1 to about 1.0% w/w, about 0.1 to about 0.6% w/w, or about 0.1 to about 0.5% w/w. In preferred embodiments, the laureth-4 is present in an amount of about 0.05 to about 8% w/w, about 0.1 to about 6% w/w, about 0.5 to about 5% w/w, about 1.0 to about 4% w/w.

Preferably the topical formulations of the present invention are in one of the following forms:

An oil-in-water emulsion: The product may be an emulsion comprising a discrete phase of a hydrophobic component and a continuous aqueous phase that includes water and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) to help to stabilize the emulsion.

A hydrophilic or hydrophobic ointment: The compositions are formulated with a hydrophobic base (e.g. petrolatum, thickened or gelled water insoluble oils, and the like) and optionally having a minor amount of a water soluble phase. Hydrophilic ointments generally contain one or more surfactants or wetting agents A microemulsion: These are clear, thermodynamically stable isotropic liquid systems that contain oil, water and surfactants, frequently in combination with a cosurfactant. Microemulsions may be water continuous, oil continuous or bicontinuous mixtures. The formulations may optionally also contain water up to 60% by weight. Higher levels may be suitable in some compositions.

A nanoemulsion: These are isotropic dispersed systems that contain water, oil, and an emulsifier. The system may be an oily system dispersed in an aqueous system, or an aqueous system dispersed in an oily system forming droplets or oily phases of nanometric sizes. Nanoemulsions often have higher loading capacity for lipophilic active ingredients than microemulsions. Hydrophobic and hydrophilic active ingredients can also be formulated in nanoemulsion. Nanoemulsions may be formed by any suitable method known in the art, including high-pressure homogenization, microfluidization, and phase-inversion temperature.

An aerosol foam or spray: The product may be an alcohol/solvent based solution containing an emulsifying wax or an emulsion comprising a discrete phase of a hydrophobic component and a continuous aqueous phase that includes water and optionally one or more polar hydrophilic excipients as well as solvents, co-solvents, surfactants, emulsifiers, and other components. These solvent or emulsion foam concentrates may include water-soluble or water-swellable polymers that help to stabilize the emulsion and corrosion inhibitors to improve compatibility between the formulation and the package. A hydrocarbon, hydrochlorofluorocarbon (HCFC) or chlorofluorocarbon (CFC) aerosol propellant can be added to the solvent or emulsion foam concentrate in packaging designed to maintain pressure until the foam or spray product is dispensed for application.

Solvents

Compositions according to the present invention may include one or more solvents or co-solvents which modify skin permeation or the activity of other excipients contained in the formulation. Solvents include, but are not limited to acetone, ethanol, benzyl alcohol, butyl alcohol, diethyl sebacate, diethylene glycol monoethyl ether, diisopropyl adipate, dimethyl isosorbide, dimethyl sulfoxide, ethyl acetate, isopropyl alcohol, isopropyl isostearate, isopropyl myristate, N-methyl pyrrolidione, polyethylene glycol, glycerol, propylene glycol and SD alcohol.

Surfactants

Compositions according to the present invention may include one or more surfactants or co-surfactants. Surfactants include, but are not limited to short-chain alcohols, alkane diols and triols, alkyl phosphate esters, polyethylene glycols and glycol ethers, polyethylene stearyl ethers, including those sold under the tradenames Brij S2, Brij S20, Brij 721, Brij 38, Brij 52, Brij 56, and Brij W1, pyrrolidine derivatives, bile salts, sorbitan fatty acid esters and polyoxyethylene sorbitan fatty acid esters.

Moisturizers

Compositions according to the present invention may include one or more moisturizers to increase the level of hydration. The moisturizer can be a hydrophilic material including humectants or it can be a hydrophobic material including emollients. Suitable moisturizers include, but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, elastomers, ethylhexyl hydroxystearate, fatty acids, glyceryl isostearate, glyceryl laurate, glyceryl monostearate, glyceryl oleate, glyceryl palmitate, glycol distearate, glycol stearate, isopropyl palmitate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, polypropylene glycol stearyl ethers, and stearyl alcohol.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, acrylamide/sodium acryloyldimethyl taurate copolymer, carboxy vinyl copolymer, carboxymethylcellulose, carboxypolymethylene, carrageenan, guar gum, xanthan gum, hydroxyethyl cellulose, hydroxypropyl cellulose, microcrystalline wax, and methylcellulose.

Additional Components

Compositions according to the present invention may be formulated with additional components such as fillers, carriers and excipients conventionally found in cosmetic and pharmaceutical topical products. Additional components including but not limited to antifoaming agents, preservatives (e.g. p-hydroxybenzoic esters, benzyl alcohol, phenylmercury salts, chlorocresol, methylparaben, propylparaben), antioxidants (e.g., BHT, BHA, ascorbic acid, tocopherol, citric acid, propyl gallate, sodium metabisulfite), sequestering agents, stabilizers, buffers, pH adjusting agents (preferably agents which result in an acidic pH, including but not limited to gluconolatone, citric acid, lactic acid, and alpha hydroxyacids), skin penetration enhancers, skin protectants (including but not limited to petrolatum, paraffin wax, dimethicone, glyceryl monoisostearate, isopropyl isostearate, isostearyl isostearate, cetyl alcohol, potassium cetyl phosphate, cetyl behenate and behenic acid), chelating agents, film formers, suspending agents (e.g., xantham gum), dyes, pigments, diluents, bulking agents, fragrances, aerosol producing agents and other excipients to improve the stability or aesthetics, may be added to the composition.

Compositions according to the present invention may be formulated with additional active agents depending on the conditions being treated. Exemplary additional active agents for a combination topical drug product include corticosteroids (e.g., clobetasol, betamethasone, halobetasol, or triamcinolone), beta andrenergic antagonists (e.g., timolol), calcineurin inhibitors (e.g., tacrolimus, or pimecrolimus), methotrexate, or cyclosporine.

Administration and Dosage

The compositions according to the present invention can be administered by any suitable administration route including but not limited to cutaneously (topically), transdermally, and mucosally. In a preferred embodiment, the composition is administered topically. The composition can be administered one or more times per month, one or more times per week, or one or more times per day. In preferred embodiments, the compositions are administered one, two, or three times per day.

The topical formulations containing laureth-4 disclosed herein can result in improved skin permeation. In some instances, the increase is a 5-fold to 30-fold increase in skin permeation as compared to the same topical formulation without laureth-4 as measured by in vitro permeation testing (IVPT). In preferred embodiments, the topical formulation containing laureth-4 products a greater than 5-fold, greater than 8-fold, greater than 10-fold, greater than 15-fold, or greater than 20-fold increase in skin permeation compared to the same topical formulation without laureth-4.

EXAMPLES

While various embodiments have been described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Experimental Example 1

Formulations of the following compositions were prepared:

| Ingredients | Formulation # 1 (2019-048-55) % w/w | Formulation # 2 (2019-048-57) % w/w |
|---|---|---|
| SHR0302 | 0.5 | 0.5 |
| DMSO | 35.0 | 35.0 |
| Laureth-4 | — | 4.0 |
| Butylated Hydroxytoluene | 0.05 | 0.05 |
| Benzyl Alcohol | 2.0 | 2.0 |
| Propylene Glycol | 15.0 | 12.5 |
| PEG 200 | 15.0 | 12.5 |
| Cyclomethicone | 7.0 | 7.0 |
| Dimethicone (350 cst) | 1.0 | 1.0 |
| ST-Elastomer 10 | 2.0 | 2.0 |
| Pemulen TR 1 | 0.8 | 0.8 |
| Carbopol 974P | 1.5 | 1.5 |
| Purified Water | Q.S to 100 | Q.S to 100 |
| 25% Trolamine | pH to 5.5-5.9 | pH to 5.5-5.9 |
| 10% (w/v) HCl | pH to 5.5-5.9 | pH to 5.5-5.9 |

Experimental Example 2

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 1:
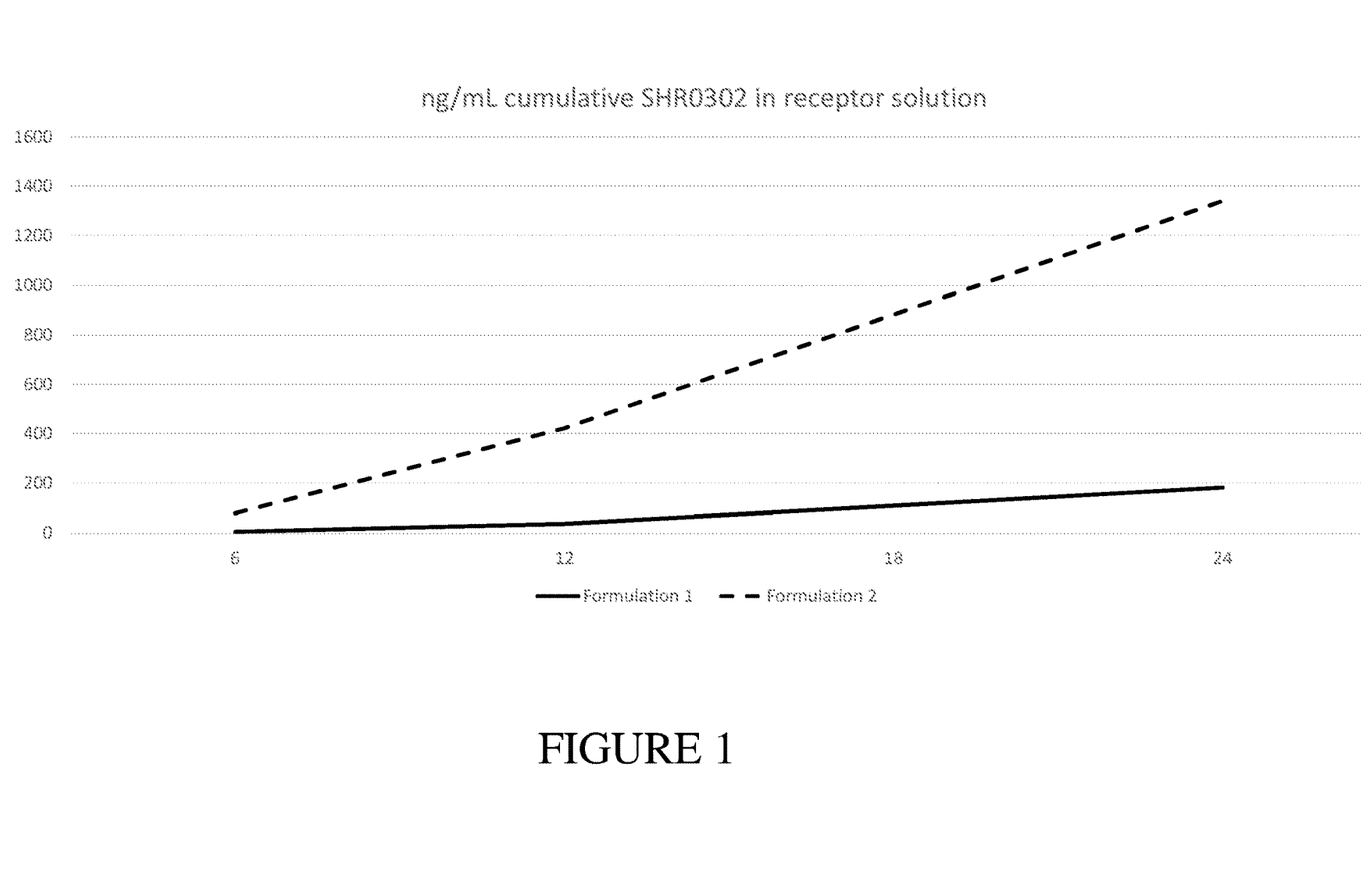
FIG. 1 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302 and DMSO.

The results of this experiment (reported as ng/mL cumulative SHR0302 in receptor solution) are shown in Table 1 and depicted in FIG. 1. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the inventive topical formulations.

TABLE 1

| Formulation # | 1 hr | 3 hr | 6 hr | 12 hr | 24 hr | Epidermis 24 hr | Dermis 24 hr |
|---|---|---|---|---|---|---|---|
| 1 | 0.0 | 0.3 | 4.7 | 36.5 | 182.5 | 71.3 | 125.6 |
| 2 | 0.0 | 8.1 | 79.4 | 423.3 | 1340.6 | 52.9 | 435.5 |

Experimental Example 3

Formulations of the following compositions were prepared:

| Ingredient | Formulation # 3 (BR18034A) % w/w | Formulation # 4 (2019-006-27) % w/w | Formulation # 5 (2019-048-59) % w/w |
|---|---|---|---|
| SHR0302 | 0.3 | 0.3 | 0.3 |
| N-Methyl-2-Pyrriolidone | 20.0 | 20.0 | 20.0 |
| Laureth-4 | 4.0 | 0.1 | 4.0 |
| Butylated Hydroxytoluene | 0.05 | 0.05 | 0.05 |
| Methylparaben | 0.2 | 0.2 | 0.2 |
| Propylparaben | 0.05 | 0.05 | 0.05 |
| Crodafos CES | 10.0 | 10.0 | 10.0 |
| Isopropyl Palmitate | 5.0 | 5.0 | 5.0 |
| White Petrolatum (Protopet 1 S) | 5.0 | 5.0 | 5.0 |
| Propylene Glycol | 15.0 | 15.0 | 15.0 |
| PEG 200 | 15.0 | 15.0 | 15.0 |
| 1N Sodium Hydroxide | 3.5 | 3.5 | 3.5 |
| Xanthan Gum | — | 0.2 | 0.2 |
| Purified Water | Q.S to 100 | Q.S to 100 | Q.S to 100 |
| 10% Sodium Hydroxide | pH to 5.5-5.9 | pH to 5.5-5.9 | pH to 5.5-5.9 |

Experimental Example 4

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% BSA in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 2:
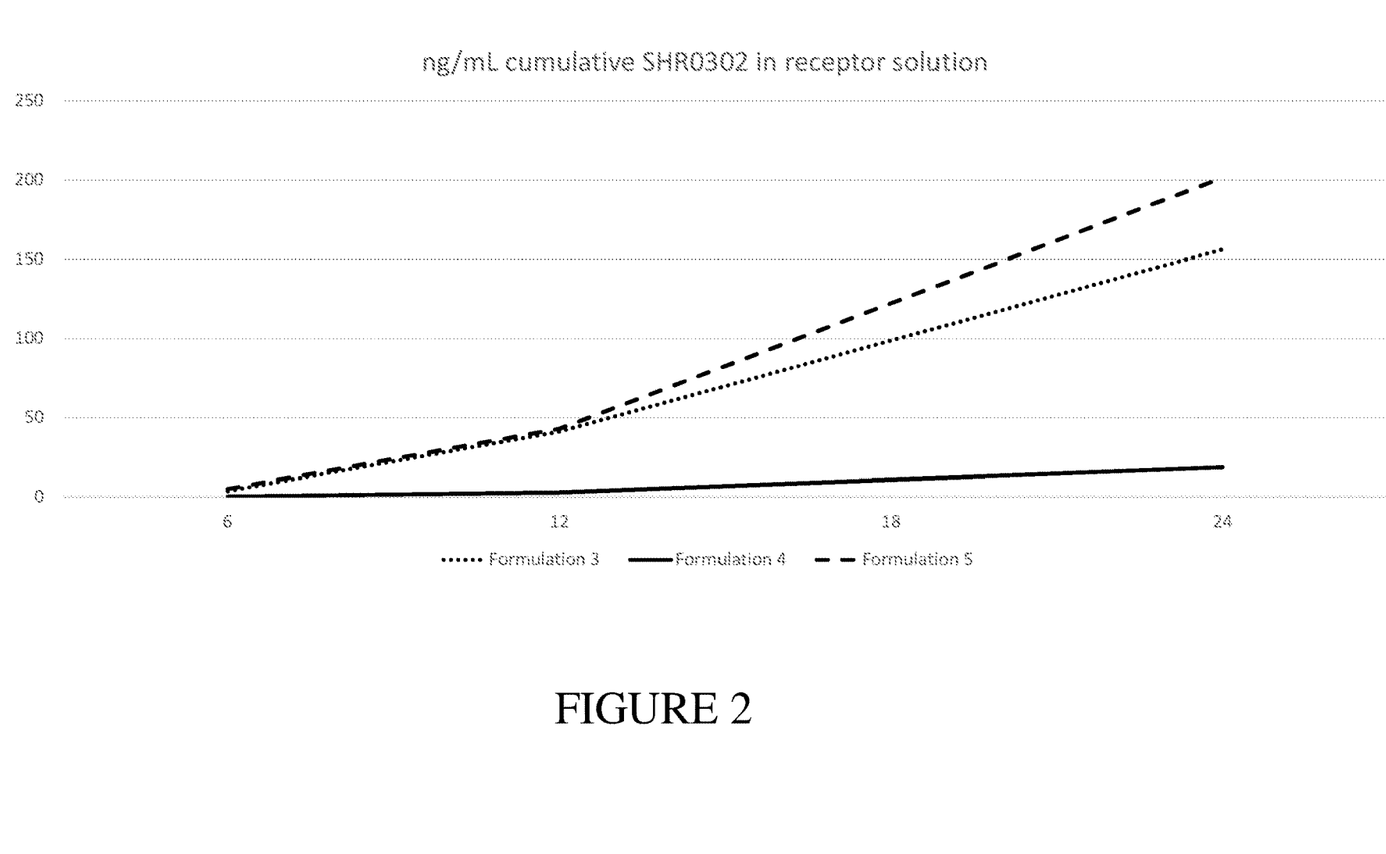

The results of this experiment (reported as ng/mL cumulative SHR0302 in receptor solution) are shown in Table 2 and depicted in FIG. 2. The addition of laureth-4 to the topical formulation containing NMP showed a surprising and striking increase in skin penetration when compared to a nearly identical formulation with minimal amounts laureth-4. These results demonstrate the efficacy of laureth-4 as a skin penetration enhancer in the inventive topical formulations.

TABLE 2

| Formulation # | 1 hr | 3 hr | 6 hr | 12 hr | 24 hr | Epidermis 24 hr | Dermis 24 hr |
|---|---|---|---|---|---|---|---|
| 3 | 0 | 0.5 | 3.5 | 41.1 | 156.4 | 15 | 63 |
| 4 | 0 | 0 | 0.1 | 2.7 | 18.4 | 33.1 | 15.0 |
| 5 | 0 | 0.6 | 4.8 | 42.8 | 201.2 | 25.9 | 62.3 |

Experimental Example 5

Formulations of the following compositions were prepared:

| Ingredients | Formulation #6 % w/w | Formulation #7 (2020-092-47) % w/w |
|---|---|---|
| SHR0302 | 0.5 | 0.5 |
| Sodium Phosphate Monobasic, Anhydrous | 0.5 | 0.5 |
| Methylparaben | 0.1 | 0.1 |
| Propylparaben | 0.02 | 0.02 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Polysorbate 60 | 10.0 | 10.0 |
| Hydroxyethyl Cellulose | 0.5 | 0.5 |
| Laureth 4 | — | 4.0 |
| Crodafos CES | 10.0 | 10.0 |
| White Petrolatum | 10.0 | 10.0 |
| Dimethicone, 350 cst | 1.0 | 1.0 |
| Purified Water | Q.S. to 100 | Q.S. to 100 |

Experimental Example 6

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 3:
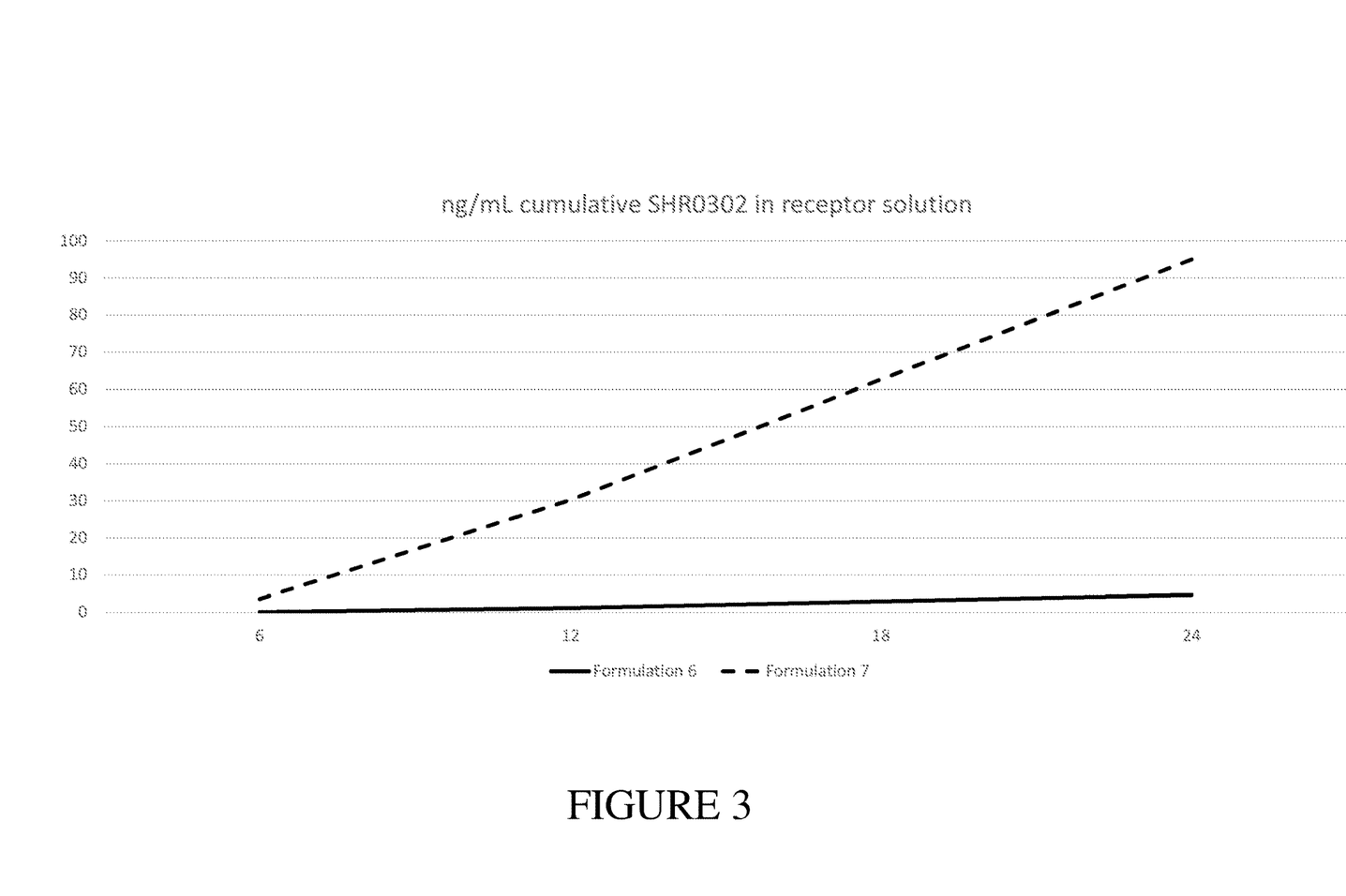

The results of this experiment (reported as ng/mL cumulative SHR0302 in receptor solution) are shown in Table 3 and depicted in FIG. 3. The addition of laureth-4 to the topical formulation containing a 1:1:1 ratio of DMSO:DMI:DEGEE showed a surprising and striking increase in skin penetration when compared to a nearly identical formulation without laureth-4. These results demonstrate the efficacy of laureth-4 as a skin penetration enhancer in the inventive topical formulations.

TABLE 3

| Formulation # | 1 hr | 3 hr | 6 hr | 12 hr | 24 hr | Epidermis 24 hr | Dermis 24 hr |
|---|---|---|---|---|---|---|---|
| 6 | 0.0 | 0.0 | 0.0 | 1.1 | 4.6 | 22.8 | 10.0 |
| 7 | 0.0 | 0.0 | 3.5 | 62.6 | 95.0 | 155.2 | 115.1 |

Experimental Example 7

Formulations of the following compositions were prepared:

| Ingredients | Formulation #8 % w/w | Formulation #9 (2020-092-61) % w/w |
|---|---|---|
| SHR0302 | 0.5 | 0.5 |
| Sodium Phosphate Monobasic, Anhydrous | 0.5 | 0.5 |
| Glycerin | 5.0 | 5.0 |
| Methylparaben | 0.1 | 0.1 |
| Propylparaben | 0.02 | 0.02 |
| Butylated hydroxytoluene | 0.05 | 0.05 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Xanthan Gum | 0.2 | 0.2 |
| Laureth 4 | — | 4.0 |
| Polyethylene (2) stearyl ether | 5.0 | 5.0 |
| Polyethylene (21) stearyl ether | 5.0 | 5.0 |
| Cetostearyl Alcohol | 6.0 | 6.0 |
| PPG 15 Stearyl Ether | 5.0 | 5.0 |
| Purified Water | Q.S to 100 | Q.S to 100 |

Experimental Example 8

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 4:
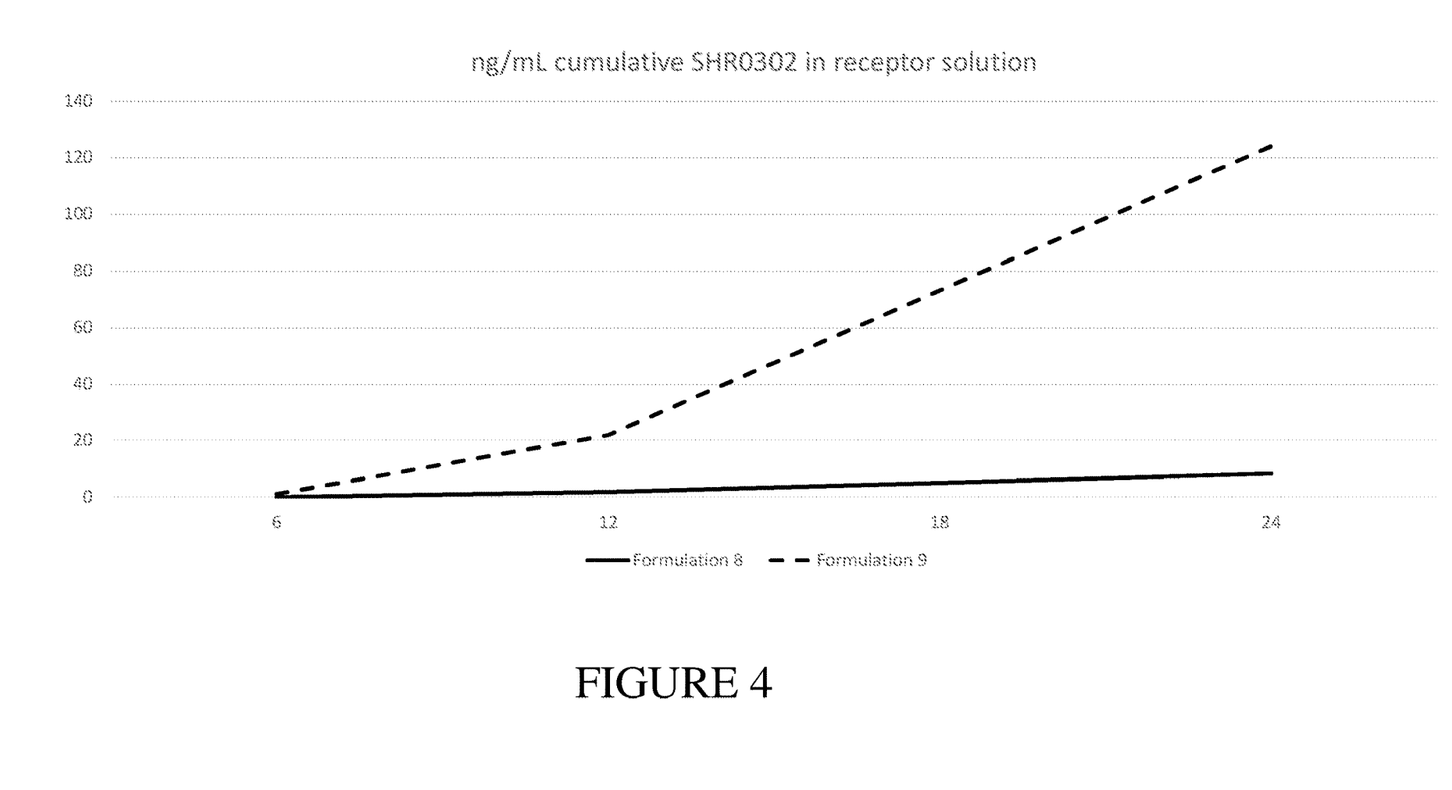

The results of this experiment (reported as ng/mL cumulative SHR0302 in receptor solution) are shown in Table 4 and depicted in FIG. 4. The addition of laureth-4 to the topical formulation containing a 1:1:1 ratio of DMSO:DMI:DEGEE showed a surprising and striking increase in skin penetration when compared to a nearly identical formulation without laureth-4. These results demonstrate the efficacy of laureth-4 as a skin penetration enhancer in the inventive topical formulations.

TABLE 4

| Formulation # | 1 hr | 3 hr | 6 hr | 12 hr | 24 hr | Epidermis 24 hr | Dermis 24 hr |
|---|---|---|---|---|---|---|---|
| 8 | 0.0 | 0.0 | 0.0 | 1.8 | 8.3 | 41.5 | 27.2 |
| 9 | 0.0 | 0.0 | 1.1 | 21.9 | 124.3 | 191.4 | 119.6 |

Experimental Example 9

Formulations of the following compositions were prepared:

| Ingredients | Formulation # 10 % w/w | Formulation # 11 % w/w |
|---|---|---|
| SHR0302 | 0.5 | 0.5 |
| DMSO | 30.0 | 30.0 |
| Laureth-4 | — | 4.0 |
| Butylated Hydroxytoluene | 0.05 | 0.05 |
| Benzyl Alcohol | 2.0 | 2.0 |
| Propylene Glycol | 15.0 | 12.5 |
| PEG 200 | 15.0 | 12.5 |
| Cyclomethicone | 7.0 | 7.0 |
| Dimethicone (350 cst) | 1.0 | 1.0 |
| ST-Elastomer 10 | 2.0 | 2.0 |
| Pemulen TR 1 | 0.8 | 0.8 |
| Carbopol 974P | 1.5 | 1.5 |
| Edetate Disodium, Dihydrate | 0.05 | 0.05 |
| D-Limonene | 0.1 | 0.1 |
| Purified Water | Q.S to 100 | Q.S to 100 |
| 25% Trolamine | pH to 4.5-5.5 | pH to 4.5-5.5 |
| 10% (w/v) HCl | pH to 4.5-5.5 | pH to 4.5-5.5 |

Experimental Example 10

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 5:
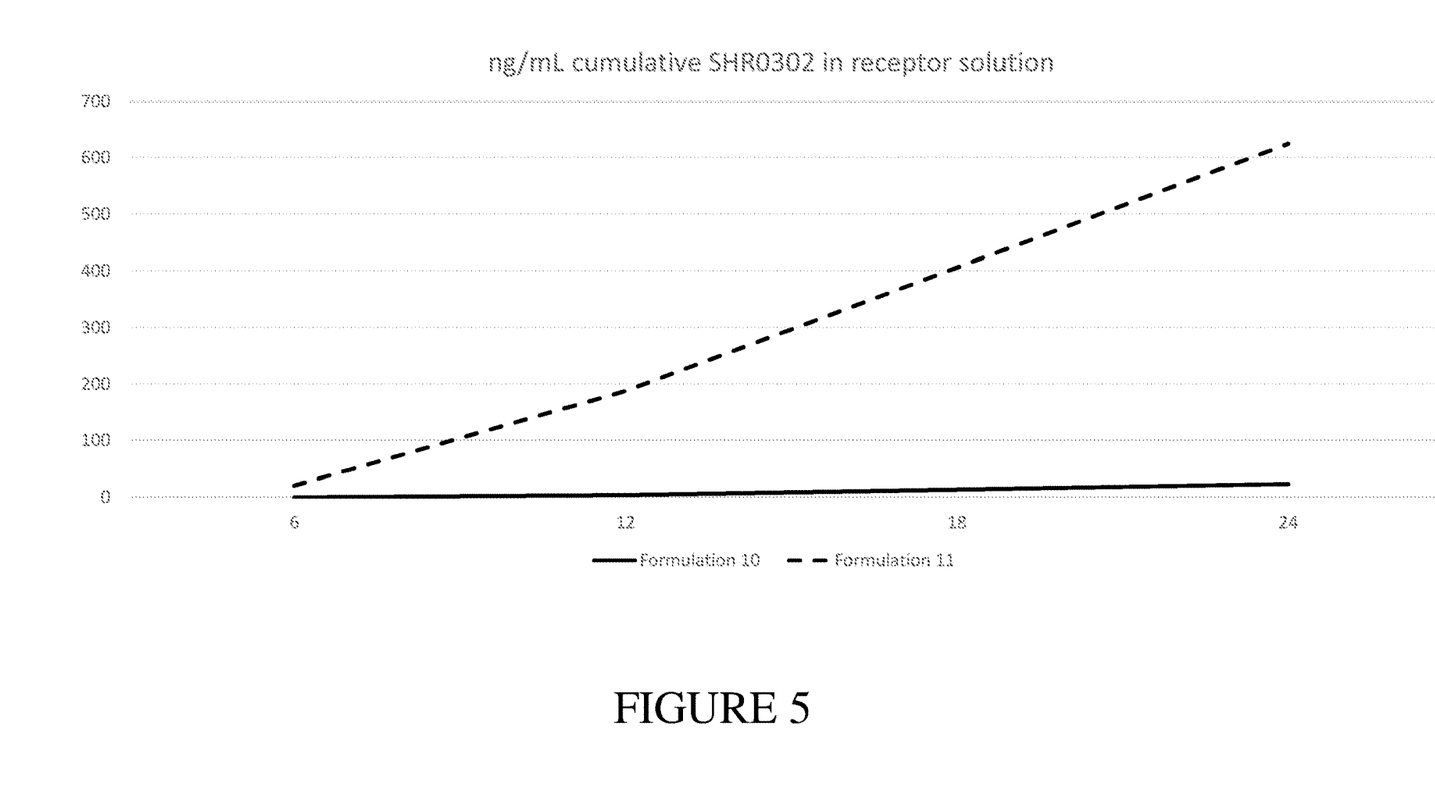

The results of this experiment (reported as ng/mL cumulative SHR0302 in receptor solution) are shown in Table 5 and depicted in FIG. 5. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the inventive topical formulations.

TABLE 5

| Formulation # | 1 hr | 3 hr | 6 hr | 12 hr | 24 hr | Epidermis 24 hr | Dermis 24 hr |
|---|---|---|---|---|---|---|---|
| 10 | 0.0 | 0.0 | 0.0 | 4.2 | 23.6 | 495.5 | 98.6 |
| 11 | 0.0 | 1.8 | 20.7 | 187.6 | 625.3 | 191.8 | 226.8 |

Experimental Example 11

Formulations of the following compositions were prepared:

| Ingredients | Formulation # 12 (2020-092-75) % w/w | Formulation # 13 (2020-092-74) % w/w |
|---|---|---|
| SHR0302 | 2.0 | 2.0 |
| DMSO | 98.0 | 94.0 |
| Laureth-4 | — | 4.0 |

Experimental Example 12

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm2 (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 6:
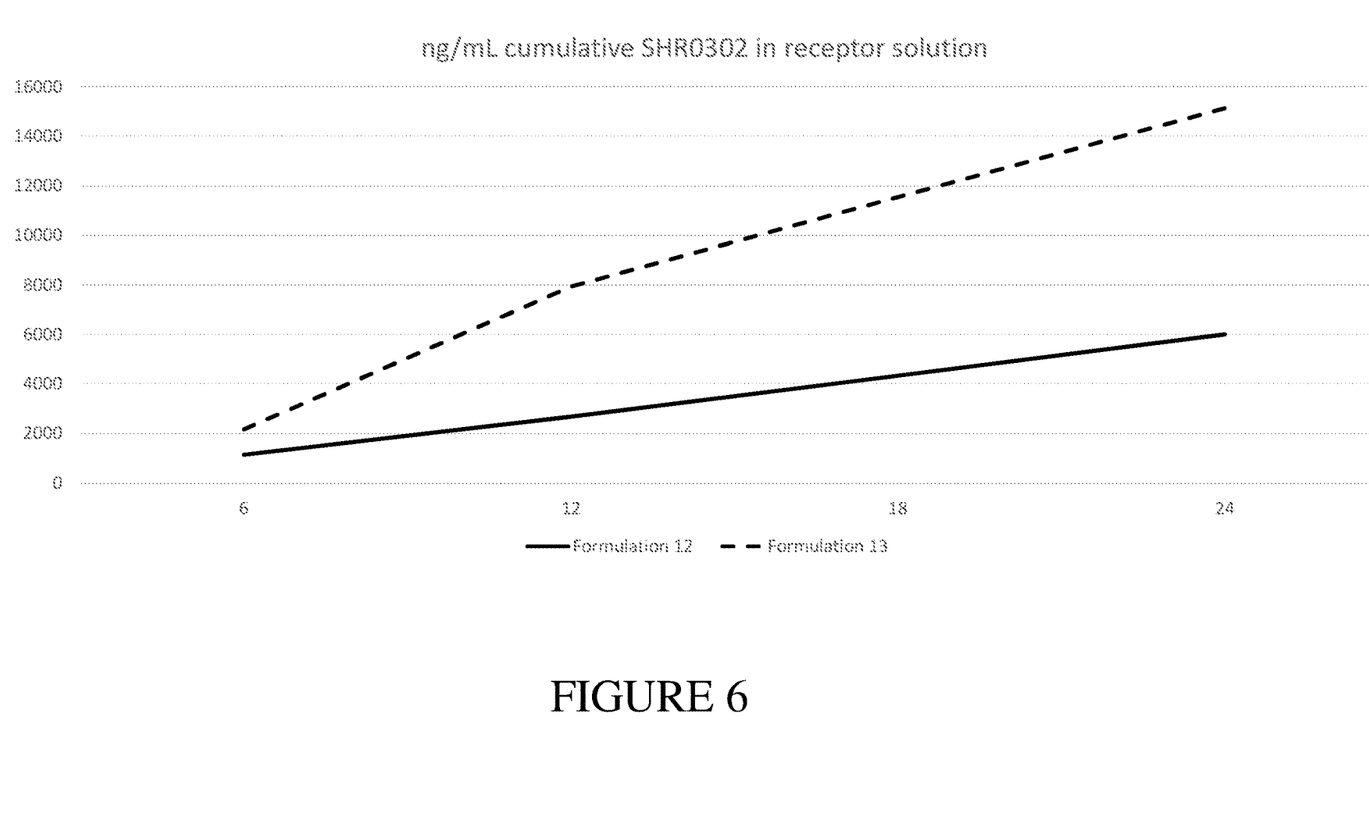

The results of this experiment (reported as ng/mL cumulative SHR0302 in receptor solution) are shown in Table 6 and depicted in FIG. 6. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the inventive topical formulations.

TABLE 6

| Formulation # | 1 hr | 3 hr | 6 hr | 12 hr | 24 hr | Epidermis 24 hr | Dermis 24 hr |
|---|---|---|---|---|---|---|---|
| 12 | 11.6 | 272.4 | 1139.6 | 2674.4 | 6008.9 | 2587 | 1899 |
| 13 | 3.6 | 324.2 | 2168.5 | 7943.5 | 15,136.0 | 2133 | 3178 |

Example 13

Formulations of the following compositions were prepared:

| Ingredients | Formulation #7 (2020-092-47) % w/w | Formulation #9 (2020-092-61) % w/w |
|---|---|---|
| SHR0302 | 0.5 | 0.5 |
| Sodium Phosphate Monobasic, Anhydrous | 0.5 | 0.5 |
| Glycerin | — | 5.0 |
| Methylparaben | 0.1 | 0.1 |
| Propylparaben | 0.02 | 0.02 |
| Butylated hydroxytoluene | — | 0.05 |
| Dimethyl Sulfoxide | 10.0 | 10.0 |
| Dimethyl Isosorbide | 10.0 | 10.0 |
| Diethylene glycol monoethyl ether | 10.0 | 10.0 |

-continued

| Ingredients | Formulation #7 (2020-092-47) % w/w | Formulation #9 (2020-092-61) % w/w |
|---|---|---|
| Polysorbate 60 | 10.0 | — |
| Xanthan Gum | — | 0.2 |
| Hydroxyethyl Cellulose | 0.5 | — |
| Laureth 4 | 4.0 | 4.0 |
| Crodafos CES | 10.0 | — |
| Polyethylene (2) stearyl ether | — | 5.0 |
| Polyethylene (21) stearyl ether | — | 5.0 |
| Cetostearyl Alcohol | — | 6.0 |
| White Petrolatum | 10.0 | — |
| PPG 15 Stearyl Ether | — | 5.0 |
| Dimethicone, 350 cst | 1.0 | — |
| Purified Water | Q.S. to 100 | Q.S to 100 |

Formulation #7 was prepared as follows: 38.93 grams of purified water was charged to the main manufacturing vessel. 0.50 grams of sodium phosphate monobasic, anhydrous was added to the water in the main manufacturing vessel and mixed until a clear solution was obtained. In a separate container labeled "Part B" 10.04 grams dimethyl sulfoxide, 10.16 grams of diethylene glycol monoethyl ether (Transcutol P®) and 10.14 grams dimethyl isosorbide were blended together. Two preservatives (0.10 grams of methylparaben and 0.021 grams of propylparaben) and 0.62 grams of the JAK inhibitor SHR0302 were added to "Part B" and stirred until completely dissolved. The entire contents of the container labeled "Part B" was added to the main manufacturing vessel and mixed until a clear solution was obtained. Polysorbate 60 was added (10.15 grams) to the main manufacturing vessel and mixed to form a hazy viscous liquid. Hydroxypropyl cellulose (0.51 grams) was added to the main manufacturing vessel and mixed to form a hazy viscous liquid. In a separate container labeled "Part E" 10.15 white petrolatum, 10.16 grams Crodafos™ CES, and 4.0 grams laureth-4 were combined and heated to 66° C. The main manufacturing vessel was heated to 68° C. Using a homogenizer (25 mm head set at 10,230 rpm) the entire contents of "Part E" were added to the main manufacturing vessel and homogenized for 5 minutes. Dimethicone (1.01 grams) was added to the main manufacturing vessel and homogenized for 2 additional minutes. Purified water (0.76 grams) was added to Q.S. ad the batch to 100%.

Formulation #9 was prepared as follows: 38.63 grams of purified water was charged to the main manufacturing vessel. Glycerin (5.1 grams) and 0.50 grams of sodium phosphate monobasic, anhydrous was added to the water in the main manufacturing vessel and mixed until a clear solution was obtained. Xanthan gum (0.2 grams) was added to the main manufacturing vessel and mixed for 59 minutes. In a separate container labeled "Part D" 10.08 grams dimethyl sulfoxide, 10.10 grams of diethylene glycol monoethyl ether (Transcutol P®), 10.06 grams dimethyl isosorbide 0.10 grams methylparaben, 0.020 grams propylparaben, 0.052 grams butylated hydroxytoluene and 0.62 grams of the JAK inhibitor SHR0302 were combined and mixed until forming a clear solution. In a third separate container labeled "Part C" 5.15 grams Polyethylene (2) stearyl ether, 5.06 grams Polyethylene (21) stearyl ether, 5.06 grams PPG 15 stearyl ether, 6.10 grams cetostearyl alcohol and 4.06 grams laureth-4 were combined and heated to 72° C. The main manufacturing vessel was heated to 74° C. Using a homogenizer (25 mm head set at 9800 rpm) the entire contents of "Part C" were added to the main manufacturing vessel and homogenized for 3 minutes. With continuous homogenization, the entire contents of "Part D" were slowly added to the main manufacturing vessel. Total homogenization time was 5 minutes. Additional purified water for this specific batch was not used to Q.S. ad the batch to 100%.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A topical pharmaceutical composition comprising SHR0302, laureth-4, and a solvent, wherein the pharmaceutical composition does not contain an additional active ingredient.

2. The topical pharmaceutical composition of claim 1, wherein the SHR0302 is present in an amount of about 0.1 to about 1.0% w/w.

3. The topical pharmaceutical composition of claim 1, wherein the laureth-4 is present in an amount of about 0.5 to about 5% w/w.

4. The topical pharmaceutical composition of claim 1, further comprising dimethyl sulfoxide.

5. The topical pharmaceutical composition of claim 1, further comprising an antioxidant, a preservative, an emulsifier, a moisturizer, or a thickener.

6. The topical pharmaceutical composition of claim 1, wherein said composition is selected from the group consisting of an oil-in-water emulsion, a water-in-oil emulsion, a microemulsion, a nanoemulsion, a foam, a spray, a hydrophilic ointment, or a hydrophobic ointment.

7. The topical pharmaceutical composition of claim 1, wherein skin penetration of the topical pharmaceutical composition is enhanced by 5-fold to 30-fold relative to the same topical pharmaceutical formulation without laureth-4 as measured by in vitro permeation testing in excised human cadaver skin dermatomed to a target thickness of 500 microns.

8. A method of treating an inflammatory skin disease, disorder, or condition in a subject in need thereof, comprising:
   topically administering to the subject a pharmaceutical composition comprising SHR0302, laureth-4, and a solvent, wherein the pharmaceutical composition does not contain an additional active ingredient.

9. The method of claim 8, wherein said inflammatory skin disease, disorder, or condition is atopic dermatitis, rosacea, psoriasis, seborrheic dermatitis, vitiligo, eczema, or alopecia areata.

10. The method of claim 8, wherein the pharmaceutical compositions is administered to the subject one or more times per day.

11. The method of claim 8, wherein the SHR0302 is present in the pharmaceutical composition in an amount of about 0.1 to about 1.0% w/w.

12. The method of claim 8, wherein the laureth-4 is present in the pharmaceutical composition in an amount of about 0.5 to about 5% w/w.

13. The method of claim 8, wherein the pharmaceutical composition further comprising dimethyl sulfoxide.

14. The method of claim 8, wherein skin penetration of the topical pharmaceutical composition is enhanced by 5-fold to 30-fold relative to the same topical pharmaceutical formulation without laureth-4 as measured by in vitro permeation testing in excised human cadaver skin dermatomed to a target thickness of 500 microns.

15. A method for enhancing the skin penetration in a human subject of a topical pharmaceutical formulation comprising:
   preparing a formulation comprising SHR0302, laureth-4 and a solvent,
   wherein the pharmaceutical composition does not contain an additional active ingredient and wherein the skin penetration of the topical pharmaceutical composition is enhanced by 5-fold to 30-fold relative to the same topical pharmaceutical formulation without laureth-4 in the subject.

16. The method of claim 15, wherein the laureth-4 is present in the pharmaceutical composition in an amount of about 0.5 to about 5% w/w.

* * * * *